(12) United States Patent  (10) Patent No.: US 9,146,003 B2
Carson  (45) Date of Patent: Sep. 29, 2015

(54) QUICK CHANGE CYLINDER BRACKET

(71) Applicant: Mustang Sampling LLC, Ravenswood, WV (US)

(72) Inventor: Howard W. Carson, Ripley, WV (US)

(73) Assignee: Mustang Sampling LLC, Ravenswood, WV (US)

( * ) Notice: Subject to any disclaimer, the term of this patent is extended or adjusted under 35 U.S.C. 154(b) by 127 days.

(21) Appl. No.: 13/898,037

(22) Filed: May 20, 2013

(65) Prior Publication Data

US 2013/0323003 A1  Dec. 5, 2013

Related U.S. Application Data

(60) Provisional application No. 61/653,851, filed on May 31, 2012.

(51) Int. Cl.
```
F16M 13/02    (2006.01)
A47B 81/00    (2006.01)
G01N 1/18     (2006.01)
G01N 1/22     (2006.01)
F16B 2/10     (2006.01)
G01N 1/10     (2006.01)
```

(52) U.S. Cl.
CPC ............. *F16M 13/02* (2013.01); *A47B 81/00* (2013.01); *G01N 1/18* (2013.01); *G01N 1/22* (2013.01); *F16B 2/10* (2013.01); *G01N 2001/105* (2013.01); *Y10T 24/44291* (2015.01)

(58) Field of Classification Search
USPC ......... 248/74.1, 74.4, 62, 311.2, 313, 316.1, 248/316.5; 24/279, 285; 285/365, 366, 367, 285/409, 410, 411
See application file for complete search history.

(56) References Cited

U.S. PATENT DOCUMENTS

| | | | |
|---|---|---|---|
| 3,603,550 A | 9/1971 | Byrd | |
| 4,437,791 A * | 3/1984 | Reynolds | 405/224.2 |
| 4,905,950 A | 3/1990 | Turner et al. | |
| 5,098,054 A | 3/1992 | Dyer | |
| 5,344,112 A | 9/1994 | Peterson et al. | |
| D385,484 S | 10/1997 | Zito | |
| 5,769,375 A | 6/1998 | Welker | |
| 6,056,332 A * | 5/2000 | Foster | 285/367 |
| D450,233 S | 11/2001 | Ward | |
| 6,672,631 B1 * | 1/2004 | Weinhold | 285/409 |
| 6,736,363 B2 | 5/2004 | Field | |
| 6,883,766 B1 | 4/2005 | Ziaylek et al. | |
| 7,032,866 B1 | 4/2006 | Braun et al. | |
| 7,287,735 B2 | 10/2007 | Heerdt et al. | |
| 7,614,593 B2 * | 11/2009 | McClure et al. | 248/229.14 |
| 7,861,982 B1 * | 1/2011 | McClure | 248/74.1 |
| 2006/0197344 A1 * | 9/2006 | Henry | 285/420 |
| 2007/0138351 A1 * | 6/2007 | Wu | 248/74.2 |

OTHER PUBLICATIONS

Grainger Industries, Battalion Square Corner Hinge, Full Mortise, PK 2—Hinges—1RBX5l1RBX5.
Grainger Industries, Battalion Adjustable Med Secondly Catch w/keeper SS—Latches—4RRK4l4RRK4.
Sawgelok Company, Bolted Plastic Clamp Supports, Part No. 304-S6-PP-32T.
Sawgelok Company, Bolted Plastic Clamp Supports, Part No. 304-S6-WPE.

* cited by examiner

*Primary Examiner* — Steven Marsh
(74) *Attorney, Agent, or Firm* — Cahn & Samuels, LLP

(57) ABSTRACT

A quick release gas sample cylinder clamp with pivoting jaws for single handed unlatching of a securely mounted sample gas cylinder upon engagement and disengagement of the battalion latch.

16 Claims, 4 Drawing Sheets

QUICK CHANGE CYLINDER BRACKET

FIELD OF INVENTION

This invention relates to an improved composite sample cylinder cabinet mounting and demounting system particularly suited for use in connection with flammable feedstock such as Liquid Natural Gas (LNG) and conforming to industry standards and regulatory codes. The invention herein facilitates one-handed unlatching of sample cylinders from a cabinet particularly useful for field switch-out of sample cylinders from a cabinet interior.

BACKGROUND

In the gas transportation and transmission fields, commonly multiple samples are extracted from a source (pipeline, tank, etc.) at certain times or at certain locations in order to assess its quality and energy content of the gas. Typically, in the context of LNG, the sample acquisition process is automatic and involves storage in discrete cylindrical sample containers for later, periodic scheduled collection by a field worker of multiple sample cylinders. The sample collection process and location of the sample cylinders preferably occur in the same environmentally controlled cabinet employed for conditioning of the LNG for sample collection such as those structures described in Applicant's U.S. Pat. Nos. 7,484,404 and 8,056,399, the subject matter of each being incorporated herein by reference.

Preferably, the cabinet structures are flammable/explosive and are constructed to conform to National Electrical Code Class 1, Division 1, Groups C and D with a T3 maximum temperature rating for North America are or with international standards such as ATEX and IEC Zone 1. Commonly, such cabinets are remotely located from the facility with instrumentation, e.g. chromatographs, employed for gas analysis. Consequently, the collection of sample cylinders requires a field worker to access the cabinet interior and swap out the full sample cylinders for new, empty cylinders. Once the full cylinders are removed from the cabinet they are taken to a facility for later analysis. Typically, a single cabinet may include several sample cylinders.

In these cases, a field worker must close the isolation valves for each cylinder and undo the mounting bracket in order to remove the sample cylinder from the cabinet interior. The undoing of a cylinder clamp and re-clamping a new sample cylinder requires the use of both hands and entails considerable effort and time. Because of the flammable/explosive content in a filled sample cylinder, particularly in the case of removal, the field worker must exercise considerable care. Where two hands are required to loosen and unclamp a filled sample cylinder from its mounting bracket, the lone field worker management of the sample cylinder is hampered when it is desirable to maintain a firm grip on the sample cylinder during the removal and substitution process. Consequently, additional assistance or an alternative adjunct to retain the now-loosened cylinder in the mounting bracket may be needed.

SUMMARY OF INVENTION

It is an object of the present invention to provide a novel quick release bracket structure for gas sample cylinders contained in a cabinet that overcomes the aforementioned problems associated with conventional structures and providing improved performance over the prior art.

Another object of the invention is to reduce the time and effort required to remove and replace sample cylinders from a protective cabinet interior.

Another object of the invention is to provide a system permitting single-handed manipulation of a gas sample cylinder securing clamp.

Another object of the invention is to reduce the labor and time associated with retrieving and replacing gas sample cylinders.

Another object of the invention is to provide a system permitting single-handed unclamping and clamping of a gas sample cylinder from a mounting array within a cabinet.

These and other objects are satisfied by A quick change sample cylinder clamping bracket comprising: a front jaw element, said front jaw element having a select length, a select width and a select depth, said front jaw element defining body having a front, face, a first side, a first shoulder, a second side, a second shoulder spaced from said first shoulder, and an aperture formed between the first and second shoulders and extending the select depth of the front jaw element, a pivotal hinge element affixed on said first side proximate to said first shoulder, a latch member affixed to said second side, said latch including a projecting hook and being moveable between a first unlocked position and a second locked position; a rear jaw element, said rear jaw element having a select length, a select width and a select depth, said front jaw element defining body having a rear face, a first side, a first shoulder, a second side, a second shoulder spaced from said first shoulder, and an aperture formed between the first and second shoulders and extending the select depth of the rear jaw element, and where said pivotal hinge element being affixed on said first side proximate to said first shoulder; a mounting rail defining a keyway; a mounting member securely connected with said rear jaw element dimensioned to be received and retained within said keyway, said mounting member including a hook engaging element for cooperating with said hook member to clamp the front jaw element to the rear jaw element; where the front and rear jaw elements are pivotable between an open, unclamped position and a locked sample cylinder clamping and retaining position when said projecting hook is cooperatively engaged with said engaging element.

Other objects are satisfied by a quick release sample cylinder mounting clamp, comprising a first jaw and a second jaw mounted together by a hinge along a first of two sides and pivotable between a closed clamping position and an open unclamping position, a battalion latch with an adjustable length hook mounted to the first jaw on the other side of the first jaw said battalion latch being capable of engaging the second jaw when the first and second jaws are pivoted to said closed clamping position, said first and second jaws defining an aperture for clampingly receiving and retaining said sample cylinder therein when said battalion latch is engaged with said second jaw and releasing said sample cylinder when said battalion latch is disengaged from the second jaw and the first jaw is pivoted away from said second jaw.

Still other objects are satisfied by the method of substituting gas sample cylinders from an environmentally controlled enclosure where each of the cylinders is mounted in a pivotable bracket with a battalion-type latch, comprising the steps of: accessing the interior of the enclosure; closing the isolation valves associated with the sample cylinders; gripping a select cylinder with one hand and releasing the battalion-type latch and pivoting the bracket clamp to the open position with the other hand; removing the sample cylinder; positioning a replacement cylinder with one hand and with the other hand; pivoting the bracket to the closed position and engaging the battalion-type latch to clamp the replacement cylinder in position; opening the isolation valves; and securing the enclosure.

The invention relates generally to a cylinder bracket that provides for single handed, fast clamping and unclamping from a cabinet interior of a gas sample cylinder. Preferably, the clamp includes a selectively actuable safety latch/keeper to avoid undesired release of a sample cylinder. The use of the invention provides for secure positional placement of a sample cylinder by clamping in select position (vertical or horizontal) for filling, empting or storing. The quick release and engagement latch mechanism permits a field worker to position and or remove the gas cylinder with one hand while manipulating (engaging or disengaging) the quick release latch with the other hand. This ease of operation leads to increased production and can improve safety when handling gas filled sample cylinders.

For definitional purposes and as used herein "connected" includes physical, whether direct or indirect, permanently affixed or adjustably mounted, as for example, the latch is connected to the body of the clamp. Thus, unless specified, "connected" is intended to embrace any operationally functional connection.

As used herein "substantially," "generally," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

In the following description, reference is made to the accompanying drawing, and which is shown by way of illustration to the specific embodiments in which the invention may be practiced. The following illustrated embodiments are described in sufficient detail to enable those skilled in the art to practice the invention. It is to be understood that other embodiments may be utilized and that structural changes based on presently known structural and/or functional equivalents may be made without departing from the scope of the invention.

DETAILED DESCRIPTION

Figure 1:
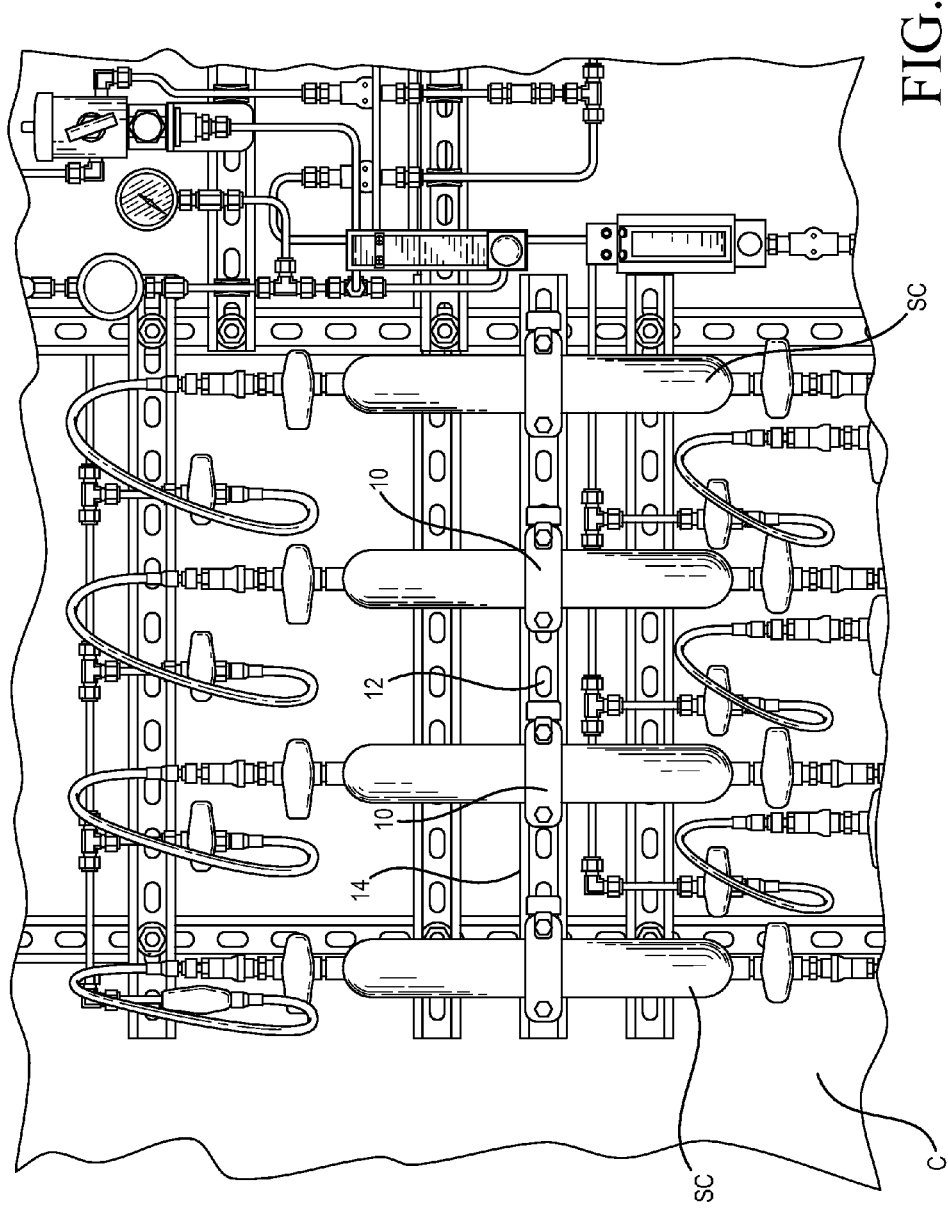
FIG. 1 is a first photographic, elevation view of a multi-cylinder array (four in this case) of vertically oriented gas sample cylinders interiorly disposed within a cabinet system and secured by the inventive quick release clamp.

FIG. 1 illustrates a portion of a sample conditioning and storage cabinet C. Cabinet C has affixed to its rear wall (that opposite the access panel/door) a rail mounted array of four, horizontally spaced, vertically disposed sample cylinders SC that are mounted within the cabinet C using quick release bracket unit assemblies 10 of the invention. In the depicted example, the sample cylinders SC are 2 inch diameter stainless steel cylinder tanks.

The novel bracket assembly unit 10 corresponds, in part, to a modified, commercially available, bolted clamp structure. Each assembly is separately mounted to a horizontally disposed rail 12 with a keyway 14 mounted to the rear wall of the cabinet.

The illustrated bracket assembly 10 features A front and rear confronting polypropylene jaw elements 16 and 18 that when aligned in an opposed relation establish an aperture/trough 15 dimensioned to clamp against, frictionally engage, and positionally secure a sample cylinder body relative to the jaws at a select distance along its axial length. The jaws are generally C-shaped defining an outwardly facing, longer side, two shorter sides approximately half the length of the longer side and ending in shoulders 17 between which a semi-circular cutout defines half of the aperture/trough 15 which define the interiorly facing side. When in the closed/clamped position, the jaws 16 and 18 form a flat square having a depth of approximately one inch.

The outwardly facing side of the front jaw element 16 features a stainless steel plate member 20 secured thereto by threaded bolts 22 having a length less than the shorter sides. The outwardly facing/back surface of rear jaw element 18 features a washer type element 24 having a diameter greater than that of the keyway 14 of the rail 12. The washer element 24 includes a cutout, forming a rearwardly projecting tongue 26 dimensioned to sit within the opening established by the keyway 14.

Along one side, the C-shaped support elements are pivotally connected with a stainless steel hinge 28 of the type available from Grainer (Model 1 RBX5) which is attached thereto respectively by short threaded screws/bolts of a length selected to avoid penetration of the aperture. The opposite side features an adjustable stainless steel battalion-type latch 30 with a hook element 32 adapted to interlock with the tongue 26 when in the closed/clamping position. The latch 30 incorporates as an additional safety feature, a keeper 34. A latch of this type is available from Grainer as Model 4RRK4. The latch 30 is securely affixed to the steel plate 20 via a bolt 22 in a manner to co-extend with the side of front jaw element 16 and adapted to pivot clear of the rear jaw element 18 when in the unlatched and opened positions.

Figure 2:
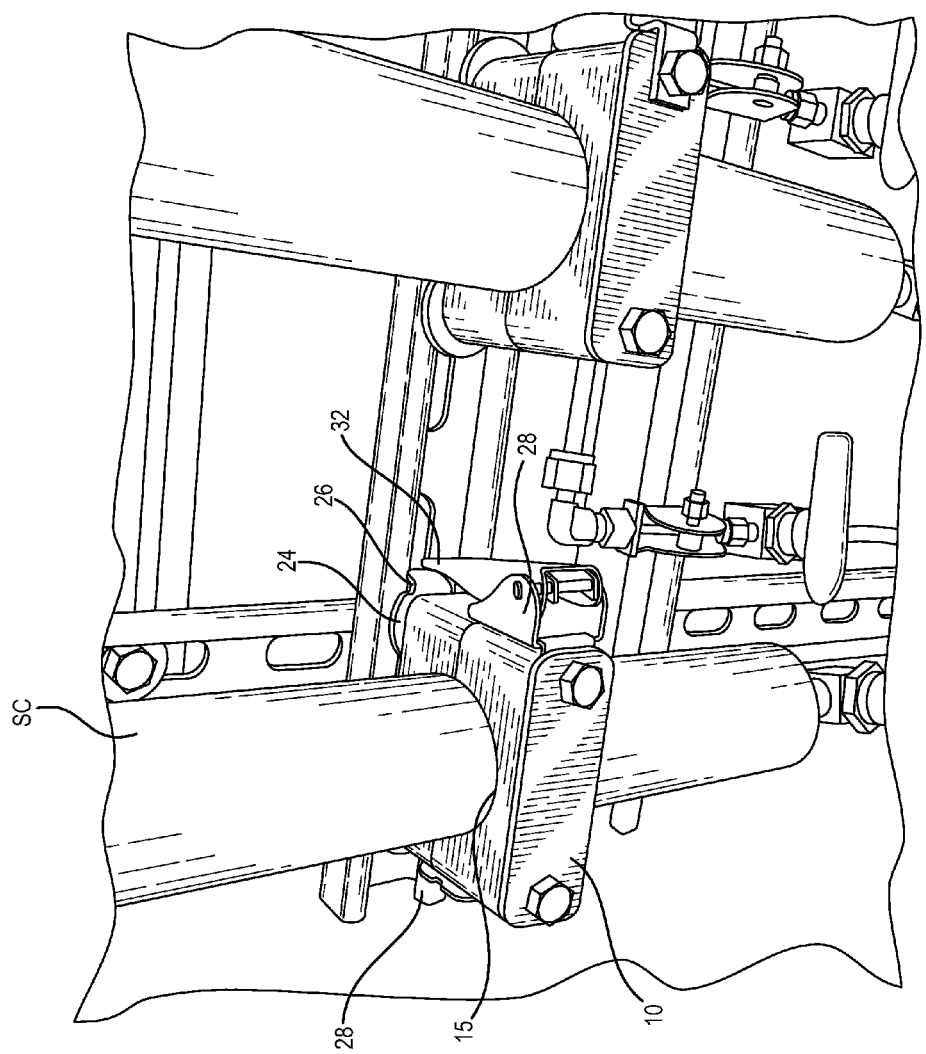
FIG. 2 is a perspective front view of a pair of sample cylinders each secured with a quick release bracket clamp embodiment of FIG. 1.
Figure 3:
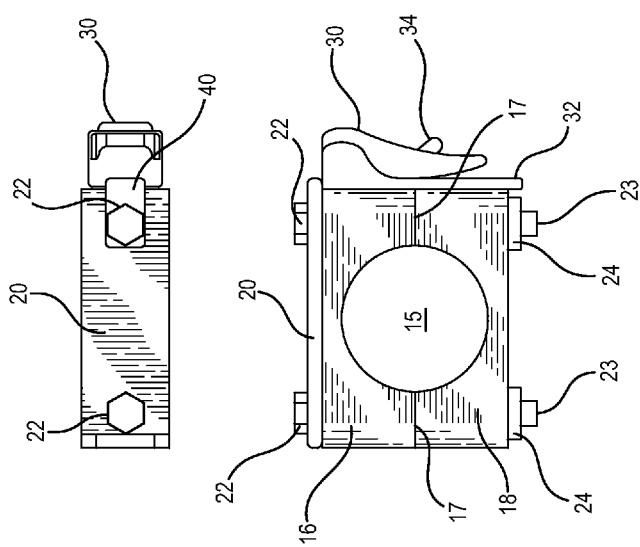
FIG. 3 is schematic drawing with a side and top view of an embodiment of quick change sample cylinder bracket invention depicted in FIG. 1.

The embodiment of latch assembly unit 10 depicted in FIGS. 1-3 is mounted to the cabinet interior by directly bolting/screwing it through the rearwardly disposed mounting rail 12, through the mounting washer and into the body of support element 18. The rail 12 is fixedly mounted within the cabinet interior at a desired location (as shown, horizontally disposed) by appropriate means such as screws, bolts or even welding. Consequently, the bracket is immovably affixed to the rail and cabinet with the tongue 26 engaged with the keyway 14. The only movement of the bracket permitted by this arrangement is pivotal between an open, unclamped position and a closed, clamped position relative to the hinge 28.

Figure 4:
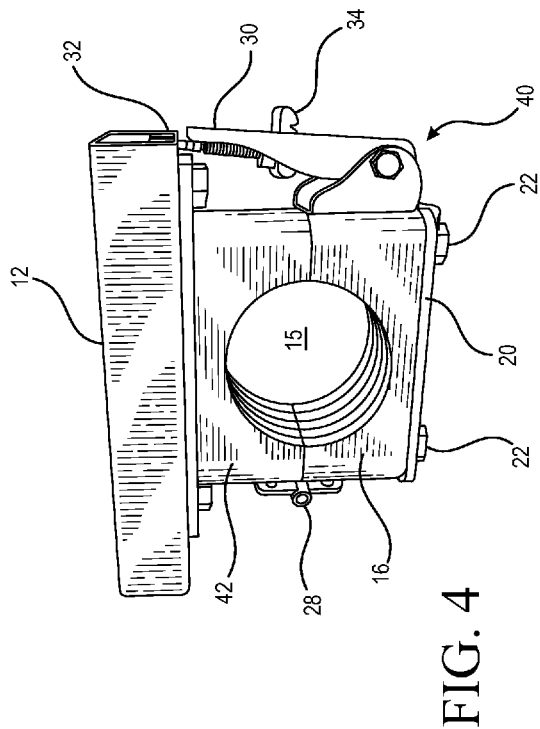
FIG. 4 is a photographic top perspective view of an embodiment of the invention in the locked/clamped position mounted to a rail.
Figure 5:
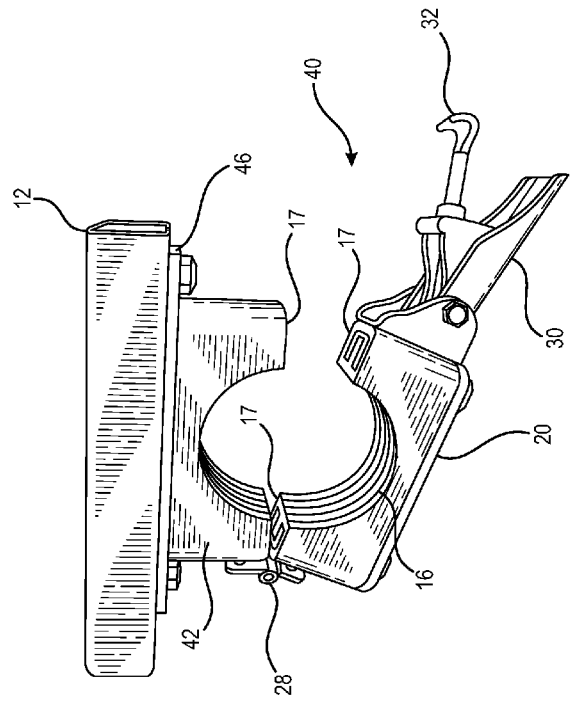
FIG. 5 is a photographic top perspective view of the embodiment of FIG. 4 in the unlocked/closed position mounted to a rail.
Figure 6:
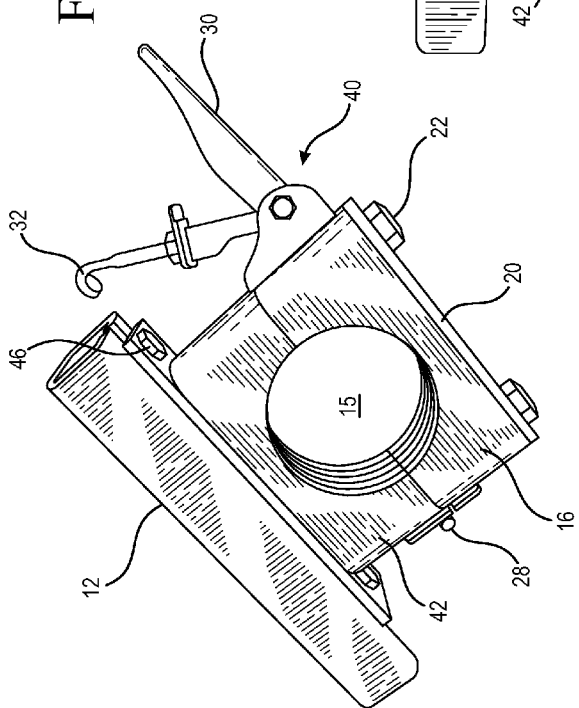
FIG. 6 is a photographic top perspective view of the embodiment of FIG. 4 in the unlocked/open position mounted to a rail.

An alternative construction entails mounting of the rear jaw element 18 to the rail is illustrated in FIGS. 4-6. The front portion of the bracket unit 40 is identical to that of the above described embodiment but in this embodiment the mounting structure associated with the rear jaw 42 differs. In this second embodiment, the bracket assembly 40 includes the rear jaw element 42 is secured to the rail by a stainless steel machined rear plate member 44. The rear plate member 44 has a width substantially corresponding to the depth of the jaw and a length that is greater than the rear wall to provide extensions for receiving bolts 46 to connect the clamping unit to the cabinet body. In a variation of this alternative, the bracket assembly may be slidably mounted to the rail by bolting the plate to a pair of washers lying in the rail keyway 14 which are connected to the bolts 46. Such an arrangement facilitates quick substitution of a bracket unit that was not performing properly. In either event, the plate extension also may serve to provide a projection for cooperating with the associated latch hook for clampingly securing a sample cylinder.

In another embodiment, associated with lighter weight cylinder containers, the bifurcated bracket jaws may be composed of a resilient elastomeric/rubber material that when brought in to the clamping position, form an aperture of slightly smaller dimensions that the perimeter of the target sample container. In this fashion, the cylinders may assume non-circular cross-sectional geometry, i.e., oval, square, etc., where the cylinders are securely clamped from the frictional engagement of the compressed resilient material forming an aperture having a geometry corresponding to the cylinder cross-section. Correspondingly, the aperture portions of the respective jaws may not be identical halves but configured in another ratio so long as the clamping force of the jaw set, when in the clamped position, satisfies the sample cylinder retaining functionality of the invention as described above.

Although only select embodiments of the invention have been disclosed in the forgoing specification, it is understood by those skilled in the art that many modifications and embodiments of the invention will come to mind to which the invention pertains, having benefit of the teaching presented in the foregoing description and associated drawing. It is therefore understood that the invention is not limited to the specific embodiments disclosed herein, and that many modifications and other embodiments of the invention are intended to be included within the scope of the invention. Moreover, although specific terms are employed herein, they are used only in generic and descriptive sense, and not for the purposes of limiting the description invention.

I claim:

1. A quick change sample cylinder clamping bracket comprising:
    a front jaw element, said front jaw element having a select length, a select width and a select depth, said front jaw element defining body having a front, face, a first side, a first shoulder, a second side, a second shoulder spaced from said first shoulder, and an aperture formed between the first and second shoulders and extending the select depth of the front jaw element, a pivotal hinge element affixed on said first side proximate to said first shoulder, a latch member affixed to said second side, said latch including a projecting hook and being moveable between a first unlocked position and a second locked position;
    a rear jaw element, said rear jaw element having a select length, a select width and a select depth, said front jaw element defining body having a rear face, a first side, a first shoulder, a second side, a second shoulder spaced from said first shoulder, and an aperture formed between the first and second shoulders and extending the select depth of the rear jaw element, and where said pivotal hinge element being affixed on said first side proximate to said first shoulder;
    a mounting rail defining a keyway;
    a mounting member securely connected with said rear jaw element dimensioned to be received and retained within said keyway, said mounting member including a hook engaging element for cooperating with said hook member to clamp the front jaw element to the rear jaw element;
    where the front and rear jaw elements are pivotable between an open, unclamped position and a locked sample cylinder clamping and retaining position when said projecting hook is cooperatively engaged with said engaging element.

2. The quick change sample cylinder clamping bracket of claim 1 where the front and rear jaws are formed from molded polypropylene and are C-shaped.

3. The quick change sample cylinder clamping bracket of claim 1 where the latch is pivotal battalion latch and includes a safety keeper to prevent unintentional unlatching.

4. The quick change sample cylinder clamping bracket of claim 3 where the latch and hinge are formed from stainless steel.

5. The quick change sample cylinder clamping bracket of claim 4 further including a first steel plate being bolted to extending the length of the front face of the front jaw and a second steel plate bolted to, extending the length of, and extending beyond the rear face, said plate being connected with said mounting member.

6. The quick change sample cylinder clamping bracket of claim 5 where the mounting member further includes a projecting tongue for clampingly engaging said projecting hook.

7. The quick change sample cylinder clamping bracket of claim 1 further comprising a second mounting member connected to said first side of said rear jaw member.

8. The quick change sample cylinder clamping bracket of claim 1 where the keyway is elongated.

9. The quick change sample cylinder clamping bracket of claim 8 where the mounting member is connected to the rear jaw with a threaded bolt.

10. The quick change sample cylinder clamping bracket of claim 1 further comprising a cabinet to which the mount rail is affixed.

11. A sample cylinder mounting clamp, comprising a first jaw and a second jaw, the second jaw including first jaw engaging surface and a second oppositely disposed mounting surface including a plate member, said first jaw and second jaw being mounted together by a hinge along a first of two sides and pivotable between a closed clamping position and an open unclamping position, a battalion latch with an adjustable length hook mounted to the first jaw said battalion latch being capable of engaging the plate member of the second jaw when the first and second jaws are pivoted to said closed clamping position, said first and second jaws defining an aperture for clampingly receiving and retaining said sample cylinder therein when said battalion latch is engaged with said second jaw and releasing said sample cylinder when said battalion latch is disengaged from the plate member of the second jaw and the first jaw is pivoted away from said second jaw.

12. The sample cylinder mounting clamp of claim 11 further comprising a mounting means for mounting said second jaw to an adjacent structure.

13. The sample cylinder mounting clamp of claim 12 where the mounting means is a mounting rail defining a keyway and the plate member of the second jaw includes a releasable interlocking member for engaging the keyway to securely connect it with said mounting rail.

14. The sample cylinder mounting clamp of claim 13 where said interlocking member is slidably mounted to said mounting rail by a pair of washers lying in the keyway and a pair of releasable bolts.

15. The sample cylinder mounting clamp of claim 14 where the first jaw defines a front face and the second jaw defines a rear face and further including reinforcing plates being bolted to the extending the length of the front face and the rear face.

16. The sample cylinder mounting clamp of claim 15 where the hinge, battalion latch, mounting means and reinforcing plates are stainless steel.

* * * * *